US011040243B2

(12) United States Patent
Chesbrough et al.

(10) Patent No.: US 11,040,243 B2
(45) Date of Patent: Jun. 22, 2021

(54) BREATHING DEVICE

(71) Applicant: Breathe With B, Inc., Chicago, IL (US)

(72) Inventors: Eric Chesbrough, Chicago, IL (US); Richard M. Chesbrough, San Diego, CA (US); Gabriel Puerto, Bay Village, OH (US)

(73) Assignee: Breathe With B, Inc., Chicago, IL (US)

( * ) Notice: Subject to any disclaimer, the term of this patent is extended or adjusted under 35 U.S.C. 154(b) by 0 days.

(21) Appl. No.: 16/358,064

(22) Filed: Mar. 19, 2019

(65) Prior Publication Data
US 2019/0290166 A1 Sep. 26, 2019

Related U.S. Application Data

(60) Provisional application No. 62/708,840, filed on Mar. 23, 2018.

(51) Int. Cl.
*A63B 23/18* (2006.01)
*A61M 21/02* (2006.01)
*A61B 5/00* (2006.01)
*A61B 5/08* (2006.01)
(Continued)

(52) U.S. Cl.
CPC ............ *A63B 23/18* (2013.01); *A61B 5/0803* (2013.01); *A61B 5/0816* (2013.01); *A61B 5/097* (2013.01); *A61B 5/486* (2013.01); *A61B 5/4836* (2013.01); *A61B 5/7435* (2013.01); *A61M 21/02* (2013.01); *A61B 5/742* (2013.01); *A61B 5/7405* (2013.01); *A61M 2021/0088* (2013.01)

(58) Field of Classification Search
None
See application file for complete search history.

(56) References Cited

U.S. PATENT DOCUMENTS

| 4,064,869 A | 12/1977 | Defares et al. |
| 4,973,047 A * | 11/1990 | Norell .................... A63B 23/18 482/13 |
| 5,363,842 A | 11/1994 | Mishelevich et al. |

(Continued)

FOREIGN PATENT DOCUMENTS

| GB | 2448212 A | 10/2008 |
| WO | 2016074042 A1 | 5/2016 |

(Continued)

OTHER PUBLICATIONS

International Search Report and Written Opinion for PCT Application No. PCT/US2019/023648, dated Jul. 24, 2019, 22 pages.

(Continued)

*Primary Examiner* — Michael R Bloch
(74) *Attorney, Agent, or Firm* — Brooks Kushman P.C.

(57) ABSTRACT

A breathing device including a housing portion and a mouthpiece portion. The housing portion has external and internal surfaces and a distal end portion and a proximal end portion. The mouthpiece portion has external and internal surfaces and includes a flared portion having a narrower distal end portion and extending to a wider proximal end portion, and the flared portion includes a depressed portion adjacent to the wider proximal end portion and configured to contact lips of a user.

21 Claims, 9 Drawing Sheets

(51) Int. Cl.
*A61B 5/097* (2006.01)
*A61M 21/00* (2006.01)

(56) References Cited

U.S. PATENT DOCUMENTS

| | | | |
|---|---|---|---|
| 5,839,435 A | 11/1998 | Matsuoka et al. | |
| 5,899,203 A | 5/1999 | Defares et al. | |
| 6,436,053 B1 | 8/2002 | Knapp, II et al. | |
| 6,554,746 B1 | 4/2003 | McConnell et al. | |
| 8,272,378 B2 * | 9/2012 | Tutsch | A63B 23/18 128/200.24 |
| 8,459,255 B2 * | 6/2013 | Spurling | A63B 23/18 128/200.24 |
| 2004/0211430 A1 * | 10/2004 | Pivovarov | A61F 5/566 128/848 |
| 2005/0128768 A1 * | 6/2005 | Martineau | G09F 9/3023 362/555 |
| 2007/0068535 A1 * | 3/2007 | Colman | A61M 16/0495 128/859 |
| 2007/0089740 A1 | 4/2007 | Baumert et al. | |
| 2007/0299354 A1 | 12/2007 | Striepe et al. | |
| 2011/0240015 A1 * | 10/2011 | Nikander | A61M 15/00 128/200.14 |
| 2013/0239655 A1 | 9/2013 | Tao et al. | |
| 2014/0246018 A1 * | 9/2014 | Terry | A61M 15/06 128/202.21 |
| 2014/0276171 A1 * | 9/2014 | Hestness | A61M 16/0493 600/531 |
| 2015/0238713 A1 | 8/2015 | Cohen et al. | |
| 2015/0258370 A1 | 9/2015 | Arkush | |
| 2015/0342518 A1 | 12/2015 | Persidsky et al. | |
| 2016/0030692 A1 * | 2/2016 | Burk | A61M 16/14 128/200.14 |
| 2016/0121062 A1 | 5/2016 | Davenport et al. | |
| 2016/0166766 A1 * | 6/2016 | Schuster | A61B 5/0022 702/54 |
| 2017/0119279 A1 | 5/2017 | Ahmad et al. | |
| 2018/0008189 A1 | 1/2018 | Wallach | |
| 2018/0008790 A1 | 1/2018 | Costella et al. | |
| 2018/0192920 A1 | 7/2018 | Rosenblood | |
| 2020/0338288 A1 | 10/2020 | Gutmark-Little et al. | |

FOREIGN PATENT DOCUMENTS

| | | | |
|---|---|---|---|
| WO | 2017071879 A1 | 5/2017 | |
| WO | 2017071964 A1 | 5/2017 | |
| WO | WO-2017071964 A1 * | 5/2017 | ......... A63B 21/0428 |

OTHER PUBLICATIONS

Blackburn, "Breath analysis: methodology towards a fieldable breath analysis device", Doctoral Thesis, Loughborough University Institutional Repository, 2011, 325 pages.

Invitation to Pay Additional Fees for Application No. PCT/US2019/023648, dated May 9, 2019, 2 pages.

Main Page for Calm—Meditation Techniques for Sleep and Stress Reduction, Available at Website: https://www.calm.com, Downloaded Mar. 18, 2019, 7 pages.

Main Page for Headspace—Meditation, Your guide to health and happiness, Available at Website: https://www.headspace.com, Downloaded Mar. 18, 2019, 3 pages.

Main Page for Muse—Technology Enhanced Meditation, Available at Website: https://www.choosemuse.com, Downloaded Mar. 18, 2019, 10 pages.

Main Page for SpireHealth—Powering the future of Remote Patient Monitoring, Available at Website: https://www.spirehealth.com, Downloaded Mar. 18, 2019, 3 pages.

Main Page for Thync—Breakthrough Bioelectronic Therapies, Available at Website: https://www.thync.com, Downloaded Mar. 18, 2019, 3 pages.

* cited by examiner

BREATHING DEVICE

CROSS-REFERENCE TO RELATED APPLICATION

This application claims the benefit of U.S. provisional application Ser. No. 62/708,840 filed Mar. 23, 2018, the disclosure of which is hereby incorporated in its entirety by reference.

TECHNICAL FIELD

The present disclosure relates to a breathing device configured to be grasped by a user's mouth and/or teeth during use.

BACKGROUND

Computer software systems have been proposed to guide users through meditative breathing sequences. These systems do not include breathing devices, but rather guide meditative sessions through audio software and apps. Other systems include wearable devices configured to improve the user's mental state. These systems do not include a breathing device configured to receive breaths of a user.

Breathing devices have been devised to train, monitor and assist the respiratory function of a human user. These devices are typically used in a medical setting where a trained professional helps the user with the breathing device to reduce issues related to the complicated nature of these devices. Other breathing devices exist in the non-medical realm, but these devices do not offer a seamless, interactive experience for the user between the breathing device and computing devices of the user.

SUMMARY

In a first embodiment, a breathing device is disclosed. The breathing device includes a housing portion having external and internal surfaces and a distal end portion and a proximal end portion. The breathing device also includes a mouthpiece portion having external and internal surfaces and including a flared portion having a narrower distal end portion and extending to a wider proximal end portion, and the flared portion including a depressed portion adjacent to the wider proximal end portion and configured to contact lips of a user. The housing portion may include a first fitting disposed on the proximal end portion of the housing portion. The mouthpiece portion may include a second fitting disposed on the narrower distal end portion of the mouthpiece portion opposing the external or internal surface of the housing portion including the first fitting on the proximal end portion. The second fitting may be configured to mate with the first fitting. The housing portion and the mouthpiece portion form a single, unitary component of the breathing device. A surface of the depressed portion may have a texture different than a surface of the remaining flared portion. The depressed portion surface may have a glossy texture and the remaining flared portion surface may have a knurled surface. The depressed portion includes first and second opposing depressed portions. The mouthpiece may be formed of an elastomeric material.

In a second embodiment, a breathing device is disclosed. The breathing device includes a housing portion having external and internal surfaces and a distal end portion and a proximal end portion. The breathing device also includes a mouthpiece portion having external and internal surfaces and a distal end portion and a proximal end portion, and the mouthpiece portion including an extending portion extending away from the proximal end portion of the mouthpiece portion and configured to contact teeth of the user. The housing portion may include a first fitting disposed on the proximal end portion of the housing portion. The mouthpiece portion may include a second fitting disposed on the distal end portion of the mouthpiece portion opposing the external or internal surface of the housing portion including the first fitting on the proximal end portion. The second fitting may be configured to mate with the first fitting. The housing portion and the mouthpiece may from a single, unitary component of the breathing device. The extending portion may include an enlarged base portion and an enlarged head portion defining a groove portion therebetween configured to contact the teeth of the user. The extending portion may be connected to the internal surface of the mouthpiece portion. The mouthpiece portion includes a number of struts connecting the extending portion to the internal surface of the mouthpiece portion.

In a third embodiment, a breathing device is disclosed. The breathing device includes a housing portion having external and internal surfaces. The housing includes a housing cavity and a series of light emitters forming a first symbol. The breathing device further includes a mouthpiece portion having external and internal surfaces and has a passage therein configured to receive breaths including inhales and exhales. The external surface of the mouthpiece portion has a texture or embossment forming a second symbol. The breathing device may further include a series of apertures formed in the housing. The series of light emitters may be aligned with the series of apertures. The first and second symbols are the same symbols. The first and second symbols may be a letter or a logo. The light emitters may be light emitting diodes (LEDs).

BRIEF DESCRIPTION OF THE DRAWINGS

FIG. 4b is a front view of the mouthpiece shown in FIG. 4a.

FIG. 4c is aside view of the mouthpiece shown in FIG. 4a.

DETAILED DESCRIPTION

Figure 1:
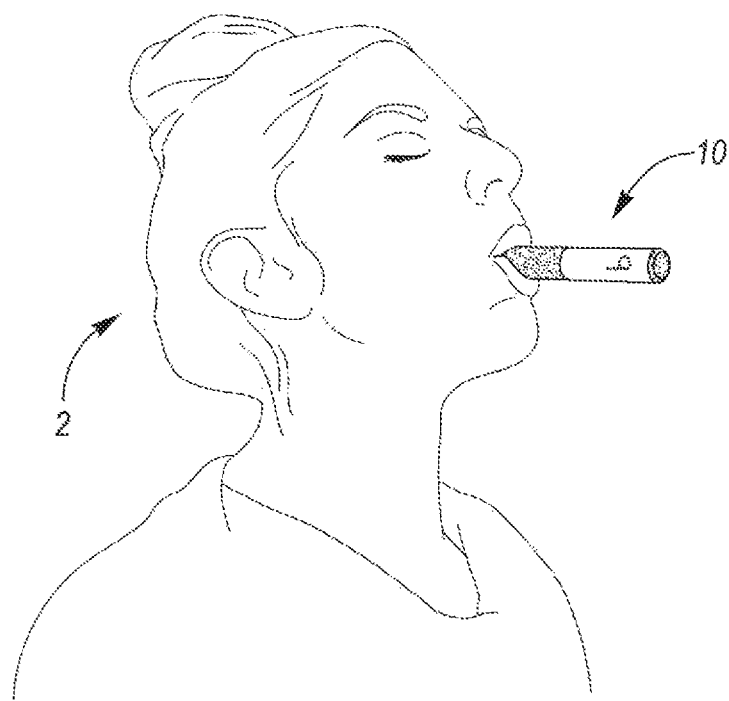
FIG. 1 depicts a perspective view of a user inhaling through a breathing device according to one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5% or 10% of the value or relative characteristic.

Computer software systems have been proposed to guide users through meditative breathing sequences. One proposal provides guided meditation resource online, accessible through a user account and a mobile app on the IPHONE and ANDROID platforms. This proposal does not use a breathing device to aid in the guided meditations. This proposal also does not provide the user feedback to help the user improve the meditation sequences. Another software proposal is configured with guided meditations to help promote sleep and reduce anxiety, stress and other distractions. This proposal uses a narrator to guide the user through relaxation sequences. Similar to the first proposal described, this proposal does not include a breathing device to guide meditations. Yet another proposal is a system and method to monitor, guide, and evaluate breathing, utilizing posture and diaphragm sensor signals. This proposal does not use a breathing device.

Other proposals that promote health and wellness include hardware devices. One such proposal includes a small, fitness tracking device configured to monitor the user's mental state. The device attaches to a pant waist band or other clothing, such as a bra. This device does not track and interact directly with a user's breathing patterns. Therefore, it does not provide a breathing device that promotes health and wellness. In another proposal, a wearable device is configured to attach to a user's forehead with flexible circuits that hook to the back of the ear and neck. The proposal also includes an app configured to connect to a smart device (e.g., IPHONE or ANDROID smartphones) via a BLUETOOTH communication device. The wearable device and app are configured to deliver pulsed neurostimulation waveform to the user to modify mental and physical state. Similar to the proposal last described, this proposal does not use a breathing device that promotes health and wellness. Yet another device has been proposed that includes a wearable headband that uses electroencephalography (EEG) to detect activity in the brain. This system is configured to inform the user of her/his brain activity to train the user's brain via audio and visual cues, such as the sound of waves. This proposal also does not offer a breathing device to interact with a user to promote health and wellness of the user.

Yet other proposals include respiratory control devices. One proposal is an inspiratory muscle training device including a chamber having an opening for the passage of air to be inhaled and exhaled, and an inlet permitting air to be inhaled to enter the chamber and to pass to the opening. In a second proposal, a respiratory muscle training device is disclosed and includes a chamber containing a variable orifice valve assembly. Another proposal includes biofeedback methods and devices suitable for providing biofeedback useful for helping a user control her/his breathing. Another proposal is a breathing training, monitoring and/or assistance device. This device includes a visual output for indicating adherence to a breathing exercise of a user. Yet another device is a pursed lip breathing device configured to provide information or feedback regarding the user's breathing. None of these proposals provide a deep interactivity with the user between a breathing device and other user device (e.g., smart phone or personal computer) to provide repeatable and sustained health and wellness. These devices also are configured such that a user uses her/his hands to grasp the device during use.

In light of the foregoing, what is needed is a breathing device and related breathing app and software that is highly interactive with the user to deliver real-time and usable feedback to the user to enhance health and wellness. What is further needed is a breathing device that is configured to be easily grasped by the mouth and/or teeth of the user without using the user's hands. This structural feature would permit the user to use her/his hands to interact with the related breathing app and software during a breathing session.

In one or more embodiments, a breathing device and related breathing app and software are disclosed. The device and related app and software are highly interactive with a user to deliver real-time and usable feedback to the user to enhance health and wellness. One or more embodiments include a breathing device that is configured to be easily grasped by the mouth and/or teeth of the user with using the user's hands. Among other benefits, this structural feature permits the user to use her/his hands to interact with the related breathing app and/or software during a breathing session.

Figure 2:
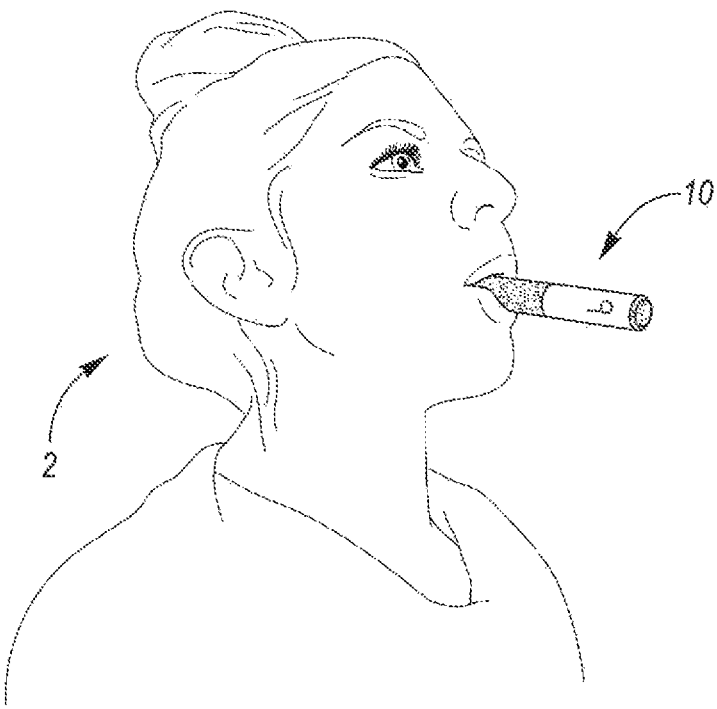
FIG. 2 depicts a perspective view of a user exhaling into the breathing device of FIG. 1 according to one embodiment.

As shown in FIGS. 1 and 2, breathing device 10 is configured to interact with user 2 during the physiological respiration process, commonly known as the breathing process. The breathing process includes inhales and exhales from user 2. The interaction between user 2 and breathing device 10 is configured to promote health and wellness of the user 2 as set forth herein. In one implementation, the interaction can be configured to permit mindful breathing of user 2 to promote health and wellness of user 2. FIG. 1 depicts a perspective view of user 2 inhaling through breathing device 10 according to one embodiment. When user 2 inhales, user 2 draws air through breathing device 10 into the mouth of user 2. FIG. 2 depicts a perspective view of user 2 exhaling into breathing device 10 of FIG. 1 according to one embodiment. When user 2 exhales, user 2 breathes air and carbon dioxide out through breathing device 10. Breathing device 10 may have the following length or in a range of any two of the following lengths: 2.0, 2.5 and 3.0 inches, such that the breathing device is light-weight and is configured to be hands-free. In another embodiment, the breathing device is configured to be grasped by the user. Breathing device may also include a bridge component to connect a mouthpiece to a housing. The bridge component may also be configured to block moisture from entering the housing and to collect debris and dust before it enters the housing.

Figure 3:
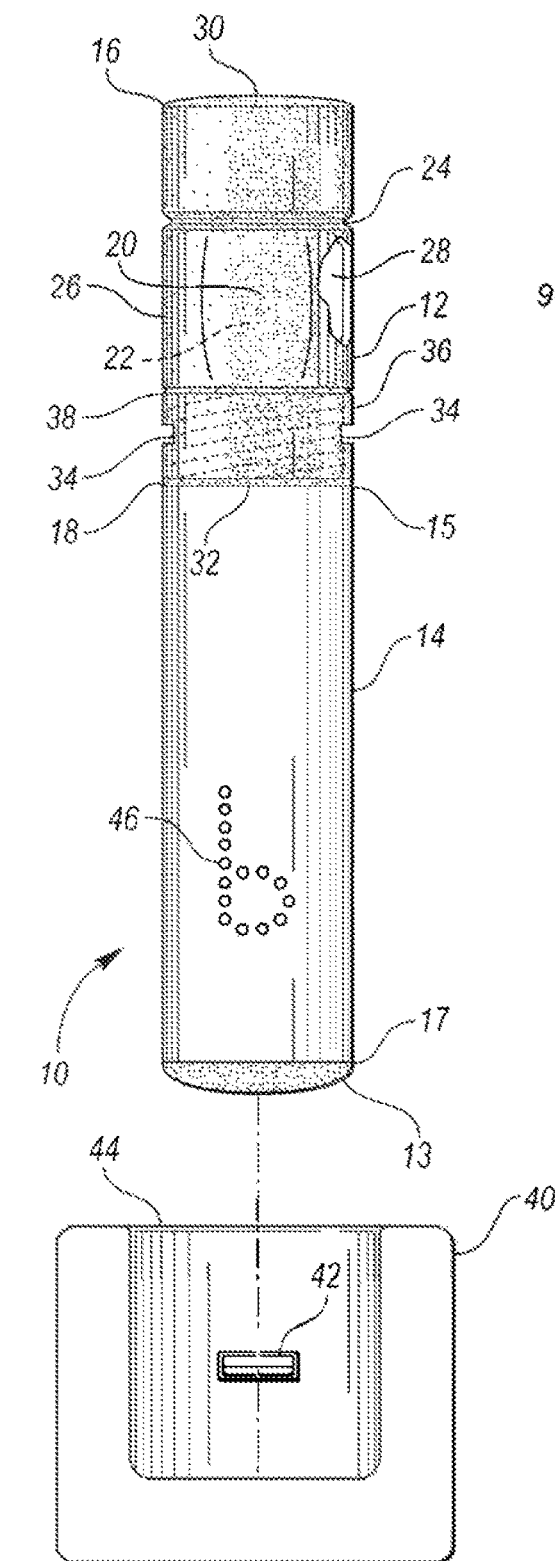
FIG. 3 depicts an elevational side view of the breathing device of FIG. 1 including a mouthpiece and a housing according to one embodiment.
Figure 4A:
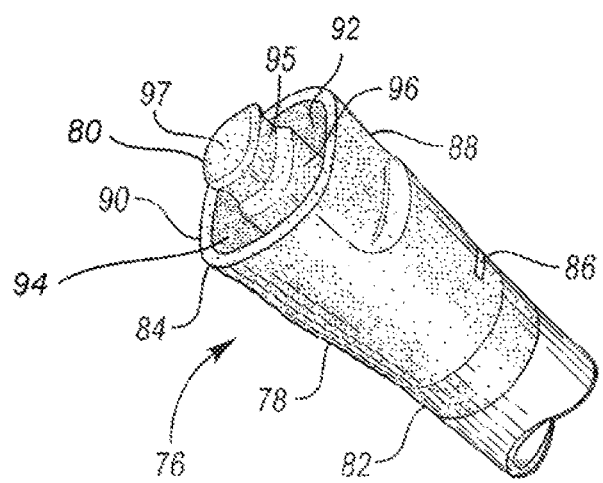
FIG. 4a is a perspective view of a mouthpiece according to a second embodiment.
Figure 4B:
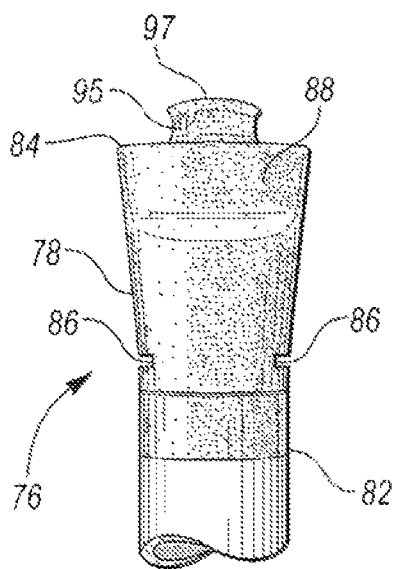
Figure 4C:
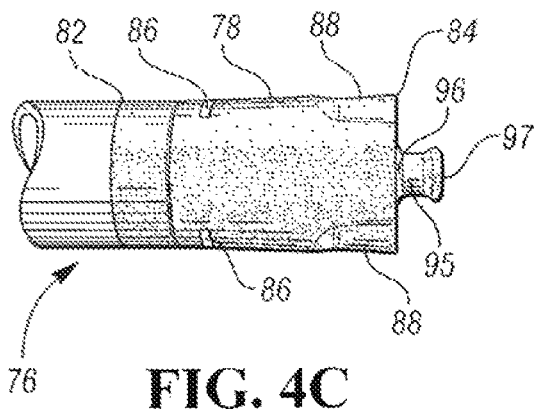
Figure 5:
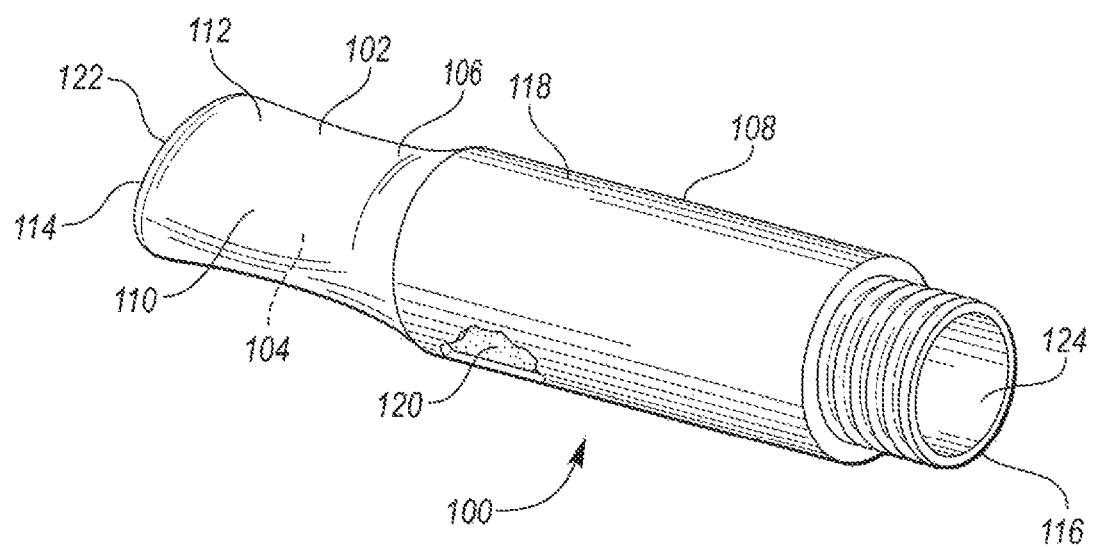
FIG. 5 depicts a perspective side view of a mouthpiece according to a third embodiment.
Figure 6:
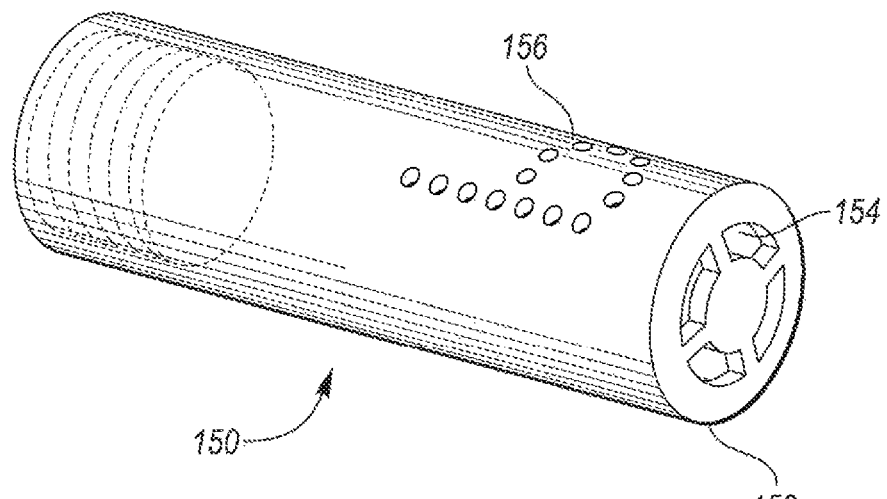
FIG. 6 depicts a perspective side view of a housing according to a second embodiment.

FIG. 3 depicts an elevational side view of breathing device 10 according to an embodiment. Breathing device 10 includes mouthpiece 12, housing 14 and end cap 13. Mouthpiece 12 includes proximal end 16 and distal end 18. Housing 14 includes proximal end 15 and distal end 17. FIGS. 4a, 4b and 4c depict perspective, plan and side views, respectively, of mouthpiece 76 according to a second embodiment. FIG. 5 depicts a perspective side view of mouthpiece 100 according to a third embodiment. FIG. 6 depicts a perspective side view of housing 150 according to a second embodiment. Mouthpiece 12, 76 and 100 are each matable to housing 14 or housing 150 to form a breathing device according to one or more embodiments. Housing 150 is matable to mouthpiece 12, 76 or 100 to form a breathing device according to one or more embodiments. In one or more embodiments, a breathing device (including breathing device 10) is configured to receive breaths (e.g., inhales and exhales) from a user and interact with the user in response to these breaths. In one embodiment, the only input into breathing device 10 is user breaths and breathing device 10 includes no other user inputs or buttons thereby lending to a seamless design. Breathing device 10 can be configured to shut off after a certain amount of time of inactivity. Breathing device 10 can be configured to turn on automatically after detecting a breath.

As shown in FIG. 3, proximal end 16 of mouthpiece 12 may be configured to be partially situated in the mouth of a user. As further described below, distal end 18 is configured to be mated to housing 14. In one embodiment, mouthpiece 12 may be formed of a polymeric material or a metal material. The polymeric material may be a polymer with viscoelasticity. Such polymers are otherwise referred to as elastomers. The elastomer may be a thermoset elastomer (such as a rubber material that is vulcanized) or a thermoplastic elastomer. The polymer material may be a hard or soft plastic material. In one or more embodiments, a hard plastic material has a glass transition temperature ($T_g$) greater than room temperature. In one or more embodiments, a soft plastic material has a $T_g$ less than room temperature. The metal material used for mouthpiece 12 may be an alloy or pure metal material. In one embodiment, the metal material may be aluminum. Mouthpiece 12 may be formed of a composite of two or more materials. For instance, mouthpiece 12 may be comolded from a hard plastic material and a soft plastic material such that the hard plastic material forms an inner layer of mouthpiece 12 and the soft plastic material forms an outer layer of mouthpiece 12. In another example, a soft plastic material may be overmolded to a hard plastic material or metal material to form mouthpiece 12.

As shown in FIG. 3, mouthpiece 12 is generally cylindrical in shape. Mouthpiece 12 includes depressed portions 20 and 22 configured to contact the lips and/or teeth of the user when using breathing device 10. Depressed portions 20 and 22 taper downward from the general cylindrical shape of mouthpiece 12 at a central portion thereof to proximal end 16 of mouthpiece 12. As shown in FIGS. 3 and 4, the sides of mouthpiece 12 extending between depressed portions 20 and 22 maintain the general cylindrical shape of mouthpiece 12. In one embodiment, the shape of the taper of depressed portion 20 mirrors the shape of the taper of depressed portion 22 relative to the longitudinal axis of mouthpiece 12. Depressed portions 20 and 22 are configured to create a shape that is easier to grasp by a user's lips and/or teeth than a cylindrical shape that is maintained along the entire longitudinal axis of a mouthpiece. In one or more embodiments, a cross-sectional area at proximal end 16 of mouthpiece 12 is less than a cross-sectional area of the cylindrical portions of mouthpiece 12.

As set forth above, FIGS. 4a, 4b and 4c depict perspective, plan and side views, respectively, of mouthpiece 76 according to a second embodiment. Mouthpiece 76 includes flared portion 78 and extending portion 80. Flared portion 78 extending from narrower end 82 toward wider end 84. Flared portion 78 includes vent 86 configured to vent gas during inhales and exhales to limit the amount of back pressure in breathing device 10, which may make user inhales and exhales more difficult. The surface of flared portion 78 may be textured. Moreover, flared portion 78 may be textured or embossed with a logo or symbol to reinforce the brand or association of breathing device 10 to the user. Flared portion 78 includes depressions 88 configured to allow the lips of a user to rest comfortably on flared portion 78. In one embodiment, the first surface finish of depression(s) 88 may be different than the second surface finish of another portion or entire remaining portion of flared portion 78. For instance, the first surface finish may be glossy, and the second surface finish may be textured (e.g., knurled, knobbed, etched, etc.). Flared portion 78 incudes wider end edge 90 forming aperture 92 in flared portion 78 to receive breaths from a user. Extending portion 80 extends through aperture 92 away from wider end 84. Extending portion 80 may be fixedly connected to flared portion 78 by struts (not shown) extending between inner surface 94 of flared portion 78 and extending portion 80. Extending portion 80 has a groove portion 95 bounded by enlarged base portion 96 and enlarged head portion 97. One or more teeth of a user may rest on groove portion 95 during use of breathing device 10. Enlarged base portion 96 and enlarged head portion 97 are configured to help maintain the one or more teeth of the user at least partially within groove portion 95. The shape of flared portion 78 and extending portion 80 are configured to cooperate with each to form a strong connection between mouthpiece 76 and a user's mouth so that the breathing device may be hands free in one or more embodiments.

As set forth above, FIG. 5 depicts another alternative mouthpiece 100. The overall shapes of mouthpieces 12 and 100 differ as described herein. Mouthpiece 100 includes depressed portions 102 and 104 configured to contact the lips and/or teeth of the user when using the breathing device. Depressed portion 102 includes first tapered portion 106 that tapers downward from the cylindrical portion 108 of mouthpiece 100 at a central portion thereof to valley portion 110 of mouthpiece 100. Mouthpiece 100 tapers upward from valley portion 110 to second tapered portion 112. The downward taper of first tapered portion 106 has an overall height greater than the upward taper between second tapered portion 112. This shaping characteristic may make it easier for a user's lips and/or teeth to grasp depressed portions 102 and 112 than a generally cylindrical shape. In one embodiment, the shape of the taper of depressed portion 102 mirrors the shape of the taper of depressed portion 104 relative to the longitudinal axis of mouthpiece 100. As shown in FIG. 5, a cross-sectional area at proximal end 114 of mouthpiece 100 may be less than a cross-sectional area of cylindrical portion 108 of mouthpiece 100.

Moving back to FIGS. 3 and 4, mouthpiece 12 includes annular groove 24 formed in a region of mouthpiece 12 that includes depressed portions 20 and 22. Annular groove 24 is configured to receive an edge portion of one or more teeth of a user. Annual groove 24 is configured to aid in locating and retaining mouthpiece 12 by the lips of the user. The depth of annular ring may be any one of the following values or in a range of any two of the following values: 0.1, 0.2, 0.3, 0.4 and 0.5 cm. The width of annular ring may be any one of the following values or in a range of any two of the following values: 0.1, 0.2, 0.3, 0.4 and 0.5 cm.

Mouthpiece 12 has external surface 26 and internal surface 28. Mouthpiece 12 also includes inlet orifice 30 at proximal end 16 and outlet orifice 32 at distal end 17. Internal surface 28, inlet orifice 30 and outlet orifice 32 define a passage within mouthpiece 12. The passage is configured to permit inhales and exhales associated with a user's breathing activities to move through the passage. During an inhale, gas moves from a region outside distal end 17 of housing 14 into housing 14 and mouthpiece 12 and from there into the mouth of the user and eventually the lungs. During an exhale, gas moves from the lungs of the user through the user's mouth and into mouthpiece 12 and housing 14 and thereby exiting through the distal end of breathing device 10. During an exhale, the shape of depressed portions 20 and 22 is configured to funnel gas from the user's mouth through outlet orifice 32 of mouthpiece 12 into housing 14. Mouthpiece 12 includes vents 34 configured to vent gas during inhales and exhales to limit the amount of back pressure in breathing device 10, which may make user inhales and exhales more difficult. Depressed portions 20 and 22 may be grasped by a user's fingers while detaching mouthpiece 12 from housing 14.

As shown in FIG. 5, mouthpiece 100 has external surface 118 and internal surface 120. Mouthpiece 100 also includes inlet orifice 122 at proximal end 114 and outlet orifice 124 at distal end 116. Internal surface 120, inlet orifice 122 and outlet orifice 124 define a passage within mouthpiece 100. The passage is configured to permit inhales and exhales associated with a user's breathing activities to move through the passage. During an inhale, gas moves from a region outside of a distal end of breathing device into the housing of the breathing device and mouthpiece 100 and from there into the mouth of the user and eventually the lungs. During an exhale, gas moves from the lungs of the user through the user's mouth and into mouthpiece 100 and the housing of the breathing device and thereby exiting the distal end of the breathing device.

As shown in FIGS. 3 and 4, mouthpiece fitting 36 is located on a portion of distal end 18 of mouthpiece 12. Fitting 36 is formed on internal surface 28 of mouthpiece 12. In other embodiments, fitting 36 may be formed on external surface 26 of mouthpiece 12. Housing fitting 38 is located on a portion of proximal end 15 of housing 14. Fitting 38 is formed on an internal surface of housing 14. In other embodiments, fitting 38 may be formed on an external surface of housing 14. In one embodiment, fittings 36 and 38 are complimentary screw threads (e.g., one female thread and the other a male thread) configured to screw into each other to connect mouthpiece 12 and housing 14. In other embodiments, the mouthpiece and housing fittings may be press fittings configured to connect mouthpiece 12 and housing 14. The mouthpiece and housing fittings may be any pair of fasteners configured to connect mouthpiece 12 and housing 14 as an integrated unit.

Beneficially, in one or more embodiments, the integrated unit, e.g., breathing device 10, may be configured to be supported solely by the user's lips and/or teeth during use such that the user does not need to further support the device using one or both hands. This beneficial aspect of one or more embodiments permits for greater interactivity with other components (e.g., computer software and app) of the disclosed systems by the user, which may lead to promoted health and wellness.

Mouthpiece 12 is also configured to be detachable from housing 14 such that a different mouthpiece can be attached to housing 14. In one example, the new mouthpiece can be a replacement for an old mouthpiece that has worn out after multiple uses. In another instance, the mouthpieces may have different patterns or color schemes and a user can switch the mouthpieces based on her/his personal preferences. In one or more embodiments, the mouthpiece does not include any mechanical or electrical components of the breathing device such that the cost of replacing the mouthpiece is reduced. In these embodiments, all the mechanical and electrical components are included with the housing. The detachability feature also permits mouthpiece 12 to be removed so that internal components of housing 14 may be repaired or replaced.

Housing 14 has a generally cylindrical shape. In one embodiment, housing 14 may be formed of a polymeric material or a metal material. The polymeric material may be a hard or rigid plastic material. In one or more embodiments, a hard plastic material has a glass transition temperature ($T_g$) greater than room temperature. The metal material used for housing 14 may be an alloy or pure metal material that has sufficient rigidity to avoid denting during use and to protect the internal components and electronics of breathing device 10. In one embodiment, the metal material may be aluminum. Mouthpiece 12 may be formed of a composite of two or more materials. For instance, a soft plastic material may be overmolded to a hard plastic material or metal material to form housing 14. In one or more embodiments, a soft plastic material has a $T_g$ less than room temperature. In one embodiment, housing 14 is constructed of an anodized aluminum shell.

As shown in FIG. 3, end cap 13 is matable to distal portion 17 of housing 14. End cap 13 may include a fitting configured to mate to a fitting disposed at distal end 17 of housing 14. In one embodiment, these fittings are complimentary screw threads (e.g., one female thread and other a male thread) configured to screw into each other to connect housing 14 and end cap 13. End cap 13 and mouthpiece 12 are removable from housing 14 so that the internal components and electronics located within housing 14 can be accessed for maintenance, e.g., battery 54 may be recharged or replaced. End cap 13 includes one or more apertures configured to ventilate gases moving through housing 14.

FIG. 6 depicts a perspective side view of housing 150 according to a second embodiment. As opposed to housing 14 that has a separate end cap 13 attached thereto, housing 150 has end portion 152 integral to housing 150. As can be seen in FIG. 6, end portion 152 includes a series of apertures 154 configured to ventilate gases flowing through housing 150. In another embodiment, end portion 152 may only include a single aperture. Housing 14 or housing 150 can be used as part of breathing device 10.

As shown in FIGS. 3 and 4, end cap 13 may be configured to support breathing device 10 on a support surface. As shown in FIG. 6, end portion 152 may be configured to support housing 150 (and therefore a breathing device) on a support surface. Either end cap 13 or end portion 152 may be configured to support a breathing device on a support surface. The outer surface of end cap 13 or end portion 150 may be flat or planar to facilitate free-standing support of a breathing device. In another embodiment, the end cap or the end portion may be curved. Housing 14 or housing 150 may include a charging port configured to receive power to charge a battery housed within housing 14 or housing 150. Breathing device 10 may be configured to be vertically oriented in charging stand 40 during a charging operation. Charging stand 40 includes charging port 42. The charging port of housing 14 or housing 150 may be configured to connect to charging port 42 during a charging operation. The charging operation may be facilitated by the shape of the outer surface of end cap 13 or end portion 152 having a shape complimentary to the shape of a bottom surface of saddle 44 of charging stand 40. In one embodiment, housing 14 is placed in charging stand 40 so that battery 54 may be recharged.

As shown in FIGS. 3 and 4, housing 14 includes a series of apertures 46. Apertures 46 are configured to direct light generated by a light source within housing 14 through apertures 46 so that the light is detectible by the user's eyes. In one embodiment, the user positions breathing device 10 such that series of apertures 46 is facing upward so that directed light is sensible by the user. As shown in FIG. 6, housing 150 includes a series of apertures 156. Apertures 156 are configured to direct light generated by a light source within housing 150 through apertures 156 so that the light is detectible by the user's eyes.

The light source may be a series of light emitters. The series of light emitters may be aligned with the series of apertures. In one embodiment, the series of light emitters includes a number of light emitters and the series of apertures includes a number of apertures, and the number of light emitters and apertures are the same, and each light emitter is arranged under a distinct aperture so that when such light emitter is illuminated, light is directed through the distinct aperture and not others. The series of apertures and/or the series of light emitters may form a symbol. In at least one embodiment, both the series of apertures and/or the series of light emitters form a symbol of the same shape. The symbol may be a shape or a logo. As shown in FIGS. 3, 4 and 6, the symbol shape is a "b" logo. The light emitters may be light-emitting diodes (LEDs). The LEDs may be miniature LEDs that have a current rating of any of the following values or in a range of any two of the following values: 1, 5, 10, 15 and 20 mA. The LED lights may be daisy-chained to create the series of light emitters. The series of light emitters may include a combination of lights having different colors. In one embodiment, the LED lights are RGB LED 3.5×2.8 mm low current RGB SMD LED. While breathing device 10 is on but idle all light emitters in series of light emitters 74 may be illuminated to show the user that the device is on.

Figure 7:
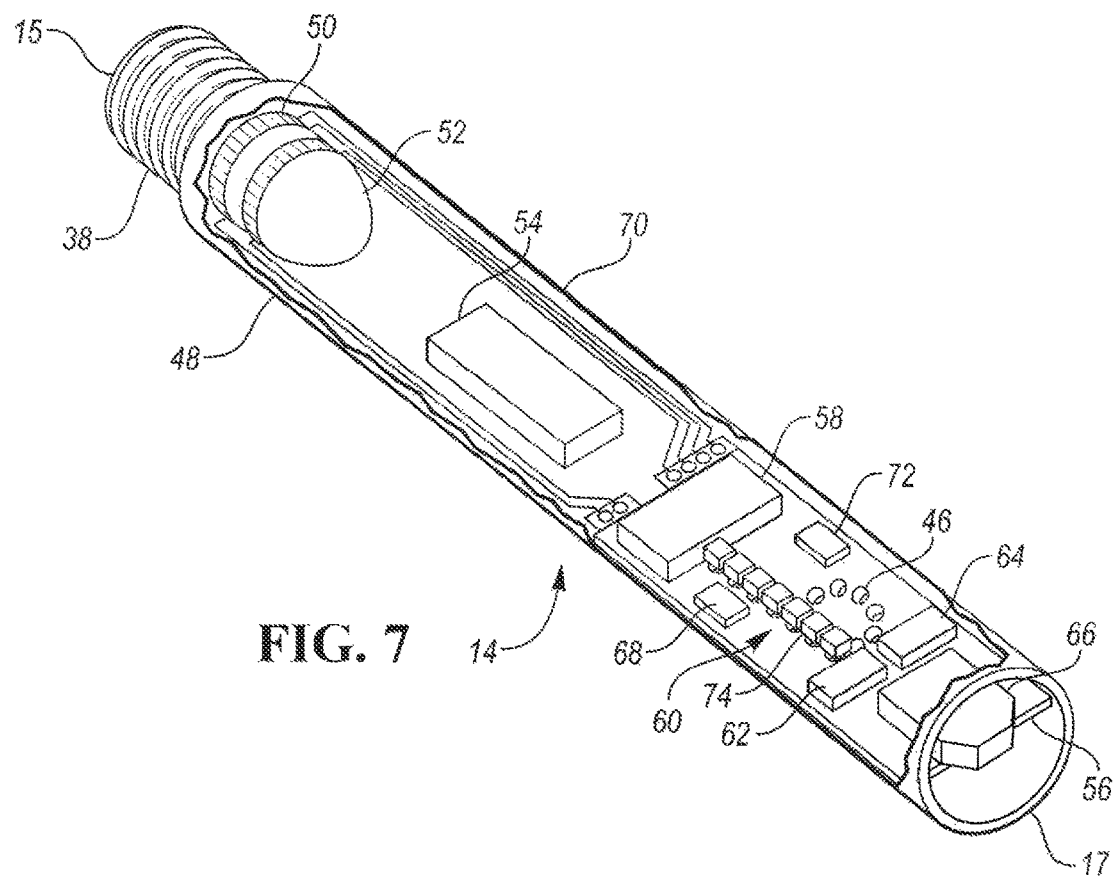
FIG. 7 depicts a partial, exploded perspective view of the housing of FIG. 3, showing internal components of the housing.

As shown in FIG. 7, housing 14 includes several components configured to provide functionality to breathing device 10 according to one or more embodiments. The components included in housing 14 may be rearranged, omitted or supplemented based on the implementation of breathing device 10. Accordingly, the layout and components shown in FIG. 7 are merely exemplary of one particular implementation.

Housing 14 defines internal cavity 48. Internal cavity 48 includes a pressure sensor 50, vibratory device 52, battery 54, and controller 56. Pressure sensor 50 is attached to the inner surface of housing 14 at a longitudinal location of housing 14 proximate to proximal end 15 of housing 14. Vibratory device 52 is attached to the inner surface of housing 14 at a longitudinal location of housing 14 adjacent pressure sensor 50 further away from proximal end 15 of housing 14. Controller 56 is attached to the inner surface of housing 14 at a longitudinal location of housing 14 adjacent distal end 17 of housing 14. Battery 54 is attached to the inner surface of housing 14 at a longitudinal location of housing 14 between vibration motor 52 and controller 56. Controller 56 also includes BLUETOOTH module 58, light emitter module 60, battery management module 62, light emitter driver 64, USB input 66 and auditory device 68. The profiles of pressure sensor 50, vibratory device 52 and battery 54 may be substantially the same. As shown in FIG. 7, the profiles are cylindrical, and the radius of the cylindrical shape is smaller than the radius of the internal cavity of the housing 14 such that passage 70 is formed to move gases from inhales and exhales. The ratio of the component radii to the internal cavity radius may be one of the following values or in the range of any two of the following values: 4:1, 3:1, 2:1 and 1:1.

Pressure sensor 50 is configured to generate a signal as a function of pressure applied to pressure sensor 50 by an inhale or exhale. Pressure sensor 50 may be an analog pressure sensor, a pressure transducer, a pressure transmitter, pressure sender, pressure indicator, piezometer or manometer. Pressure sensor 50 is configured to sense any of the following pressures or in a range of any two of the following pressures: 300, 400, 500, 600, 700, 800, 900, 1,000, 1,100 and 1,250 hPa. Pressure sensor 50 is configured to transmit pressure signals to controller 56. Pressure sensor 50 is configured to receive power either directly or indirectly from battery 54. Pressure sensor 50 is configured to send pressure signals to controller 56 and controller 56 may be configured to process these signals to determine whether an inhale, an exhale or hold is occurring and can track this status over time to determine whether an inhale period, an exhale period or a hold period has been achieved. In one embodiment, pressure sensor 50 is BMP388 digital pressure sensor available from Bosch Sensortec GmbH of Reutlingen, Germany.

Vibratory device 52 is configured to generate a vibration signal sensible by the user of breathing device 10. Vibration device 52 may be a vibration motor (e.g., a 3 volt DC vibratory motor). In some embodiments, vibration device 52 is a linear resonant actuator. In some embodiments, the vibration device 52 is configured to transmit vibration signals in the longitudinal direction and/or radial directions of housing 14. Vibratory device 52 is configured to receive signals from controller 56 so that vibratory device 52 transmits a vibratory signal as an output. The vibratory signal may make housing 14 and mouthpiece 12 vibrate such that it is sensible by the user of breathing device 10. Vibratory device 52 is configured to receive power either directly or indirectly from battery 54.

Vibratory device 52 is configured to receive a vibratory input signal from controller 56. Controller 56 is configured to transmit a signal to vibratory device 52 to direct vibratory device 52 to deliver an audio output signal to cue the user to start or end an inhale period, exhale period or hold period. Vibratory device 52 is configured to transmit different vibratory output signals having different vibratory characteristics in response to the vibratory input signals. The vibratory characteristic may be a vibratory frequency characteristic. The frequency characteristic may be tone, e.g., different tones. A first tone may be lower than a second tone. The frequency characteristic may be a number of pulses, e.g., a different number of pulses. The number of pulses may be any one of the following values or in a range of any two of the following values: 1, 2, 3, 4, 5, 10, 15 and 20. The frequency characteristic may be a duration of pulses, e.g., a different duration of pulses. The duration of pulses may be any one of the following values or in a range of any two of the following values: 0.1, 0.2, 0.3, 0.4, 0.5 and 1 second. The frequency characteristic may be a vibratory intensity. A first intensity may be higher than a second intensity such that the vibration of vibratory device 52 is more intense in relation to the first intensity. The vibratory output signal produced by vibratory device 52 may also produce sounds to provide the user audio feedback. In one or more embodiments, a first and second frequency characteristics may differ in more than one characteristic. For instance, a first frequency characteristic may differ from the second frequency characteristic in two or more of the following characteristics: tone, number of pulses, duration of pulses, and intensity. In one embodiment, a first vibratory output signal may be a 1 Tap vibration and a second vibratory output signal may be a 2 Tap vibration.

A first pitch may be lower than a second tone of a frequency-related scale. The frequency characteristic may be intensity, e.g., different intensities. A first intensity may be higher than a second intensity such that auditory device makes a louder sound in relation to the first intensity. The audio output signal produced by auditory device 68 may also include vibrations to provide the user a haptic feedback.

Battery 54 is configured to deliver power to other components, e.g., pressure sensor 50, vibratory device 52, controller 56 and auditory device 68, so that such components operate according to their performance characteristics. Battery 54 may be a rechargeable battery. In such embodiments, battery 54 is configured to receive recharging power received by USB input 66. The rechargeable battery may be a lithium-ion polymer rechargeable battery. Battery 54 may also be a nickel-metal hydride battery or a nickel-cadmium battery. The power rating of battery 54 may be any of the following values or in a range of any two of the following values: 0.4, 0.5, 0.6, 0.7, 0.8 and 0.9 wh. The voltage rating of battery 54 may be any of the following values or in a range of any two of the following values: 3.7, 4, 5 or 6 volts. In one embodiment, battery 54 may be a 3.7 volt 180 mAh LIPO battery. In other embodiments, the milliampere hours of battery 54 may be in the range of 100 to 200 mAh.

Controller 56 is configured to transmit and receive signals to other components, e.g., pressure sensor 50, vibratory device 52, BLUETOOTH module 58, light emitter module 60, battery management module 62, light emitter driver 64, USB input 66 and auditory device 68, so that such components operate according to the signals transmitted by controller 56 and controller 56 operates in response to signals received from the other components. Controller 56 may be configured to receive over the air updates through BLUETOOTH module 58 to update firmware or computer code stored in memory 72.

Controller 56 may be a printed circuit board. Other components, e.g., pressure sensor 50, vibratory device 52, BLUETOOTH module 58, light emitter module 60, battery management module 62, light emitter driver 64, USB input 66 and auditory device 68, may be mounted to the printed circuit board. The printed circuit board may be soldered to housing 14. Controller 56 may be embodied in a processor configured to carry out instructions for the methods and systems described herein. Controller 56 is configured to store data, e.g., pressure data, to memory 72. Controller 56 may be one or more computing devices configured to process commands, such as a computer processor, microprocessor, or any other device, series of devices or other mechanisms capable of performing the operations set forth herein. The memory may store instructions and commands. The instructions may be in the form of software, firmware, computer code, or some combinations thereof. The memory may be in any form of one or more data storage devices, such as volatile memory, non-volatile memory, electronic memory, magnetic memory, optical memory, or any other form of data storage device.

BLUETOOTH module 58 is configured to receive and transmit data (e.g., pressure data and breathing pattern data) over a relatively short distance using short-wavelength UHF radio waves in the industrial, scientific and medical (ISM) radio bands from 2.400 to 2.485 GHz. BLUETOOTH module 58 is a data transceiver, i.e., it is configured to receive and transmit data. BLUETOOTH module 58 may be configured to receive and/or transmit data from and to a smartphone, tablet and/or personal computer. BLUETOOTH module 58 may be compatible with any version of BLUETOOTH, including BLUETOOTH version 4.0. In one embodiment, BLUETOOTH module is a SIMBLEE programmable BLUETOOTH module, available from RF Digital Corporation of Hermosa Beach, Calif. Other examples of BLUETOOTH modules include nRF8001, nRF51822 and nRF52832 BLUETOOTH modules available from Nordic Semiconductor, Inc. of Trondheim, Norway, DA14580 and DA14680 BLUETOOTH modules available from Dialog Semiconductor (UK) Ltd. of Reading, United Kingdom, CC2540, CC2541 and CC2630/40/50 BLUETOOTH modules available from Texas Instruments Inc. of Dallas, Tex., and PSoC4 BLE and PROC 4 BLUETOOTH modules available from Cypress Semiconductor Corp. of San Jose, Calif. Controller 56 may be configured to detect an initial exhale or inhale into the device and to transmit a signal to BLUETOOTH module 58 to initiate a pairing and connection with handheld user device 202.

BLUETOOTH module 58 is an example of a technology that can be used in a personal area network (PAN) utilized by breathing device 10. Other non-limiting examples of PAN technologies include induction wireless technology using magnetic induction for close-range communications, infrared wireless technology using infrared signals for close-range communications, ultra wideband using baseband pulses applied directly to an antenna, and ZIGBEE technology, which is a lower power and cost alternative to BLUETOOTH technology.

Battery management module 62 is configured to manage the utilization of battery 54. Battery management module 62 may be configured to safely recharge a rechargeable battery 54 by monitoring the state of battery 54. One example of battery management module 62 is 1904 battery management module available from Adafruit Industries LLC of New York City, N.Y. Another example of battery management module 62 is PRT-14411 battery management module available from SparkFun Electronics of Niwot, Colo. Battery management module 62 is electrically connected to USB input 66. USB input 66 includes a socket configured to receive a USB plug (e.g., a standard size plug or a micro USB plug). When the USB plug is connected to USB input 66 and a power source, power is transmitted through the plug and USB input 66 to battery management module 62. Battery management module 62 is configured to determine whether to send the power to battery 54 to recharge it. In one embodiment, battery management module 62 is a lithium ion linear battery charger with LDO, load switches and reset generator. The load switch may be a power switch IC, e.g., a power distribution low in voltage, 1.8 amp single channel load switch.

Light emitter module 60 is configured to regulate power to series of light emitters 74. Light emitter module 60 may be a LED driver configured to provide a constant quantity of power to a series of LEDs as their electronic properties change with temperature. In one embodiment, the LED driver is the FemtoBuck LED driver available from SparkFun Electronics of Niwot, Colo. In another embodiment, the LED driver is the PicoBuck LED driver available from SparkFun Electronics of Niwot, Colo.

Controller 56 is configured to transmit light emitter signals to light emitter module 60 such that light emitter module 60 changes each light emitter in the series of light emitters 74 from one of an operational state and non-operational state to the other of the operational state and non-operational state. The operational state may be illumination of the light emitter (e.g., an "on" state) and the non-operational state may be non-illumination of the light emitter (e.g., an "off" state). The light emitter control signals may change the states of each light emitter in a pre-determined sequence. For example, light emitters can be changed from a non-operational state to an operation state by turning on one light emitter at a time in sequence and pausing for a time period before turning on the next light emitter. The pause time period may be any of the following or in a range of any two of the following values: 0.05, 0.1, 0.2, 0.3, 0.4 and 0.5 seconds. Controller 56 is configured to transmit a signal to light emitter module 60 to direct series of light emitters 74 to change operational state to cue the user to start or end an inhale period, exhale period or hold period.

Controller 56 may be further configured to transmit light emitter signals to light emitter module 60 such that light emitter module 60 changes the color and/or pulsing mode of each light emitter in the series of light emitters 74. The light emitter control signals may change the colors of each light emitter in a pre-determined sequence. For example, light emitters can be turned on in a sequence of rainbow colors (e.g., red, orange, yellow, green, blue, indigo and violet). The light emitter control signals may pulse one or more of the light emitters when on. For instance, the pulse timing may be one of the following or in a range of any two of the following values: 0.001, 0.005, 0.01, 0.05, 0.1 and 0.2 seconds. Controller 56 may be further configured to store reminders to the non-volatile memory and transmit reminders to other devices, such as a user device.

Auditory device 68 is configured to receive audio input signal from controller 56 and produce audio output signal that can be heard by a user. Controller 56 is configured to transmit a signal to auditory device 68 to direct the auditory device 68 to deliver an audio output signal to cue the user to start or end an inhale period, exhale period or hold period. The auditory device 68 is configured to transmit different audio output signals having different auditory characteristics in response to the audio input signals. The auditory characteristic may be an auditory frequency characteristic. The frequency characteristic may be tone, e.g., different tones. A first tone may be lower than a second tone. The frequency characteristic may be pitch, e.g., different pitches. A first pitch may be lower than a second tone of a frequency-related scale. The frequency characteristic may be intensity, e.g., different intensities. A first intensity may be higher than a second intensity such that auditory device 68 makes a louder sound in relation to the first intensity. The audio output signal produced by auditory device 68 may also include vibrations to provide the user a haptic feedback. Auditory device 68 may be a digital speaker, such as the Adafruit 1784 speaker available from Adafruit Industries LLC of New York City, N.Y. In one or more embodiments, a first and second frequency characteristics may differ in more than one characteristic. For instance, a first frequency characteristic may differ from the second frequency characteristic in two or more of the following characteristics: tone, pitch, and intensity. In one embodiment, auditory device 68 may be a micro audio buzzer. Controller 56 may be further configured to transmit audio content (e.g., chimes, sounds, chirps, bells, whistles, songs, audio books, reminders (e.g., calendar reminders), narrated breathing instructions from a breathing instructor, messages from social media influencers, etc.) to auditory device 68 such that auditory device 68 outputs the audio content.

Figure 8:
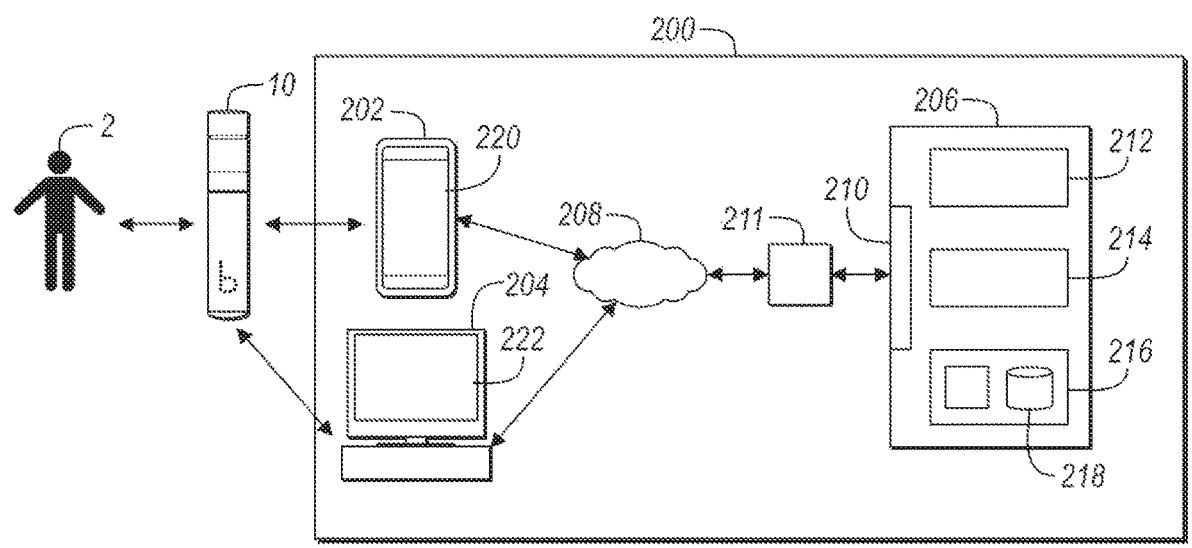
FIG. 8 illustrates an example computer system architecture for a breathing device system and method according to one embodiment.

FIG. 8 is a schematic diagram of computer system 200 configured to implement one or more embodiments. User 2 interacts with breathing device 10. Breathing device 10 is configured to permit user 2 to inhale into and exhale through breathing device 10. Breathing device 10 is further configured to inform user 2 to hold her/his breath during a hold period. Breathing device 10 is configured to transmit and receive data from handheld user device 202 and user computer 204. This communication can be carried out using BLUETOOTH technology or other wireless technology. In one embodiment, breathing device 10 and handheld user device 202 and/or user computer 204 are connected through a WiFi network. Handheld user device 202 and user computer 204 are configured to transmit and receive data from server 206 through external network 208. Server 206 includes network interface 210. Server 206 includes microprocessor 212, volatile memory 214 and non-volatile memory 216. Non-volatile memory 216 includes database 218 for storing data. Database 218 may include various kinds of mechanisms for storing, accessing, and retrieving various kinds of data, including a hierarchical database, a set of files in a file system, an application database in a proprietary format, a relational database management system (RDBMS), etc. In one embodiment, database 218 is a relational database in Microsoft SQL Server. Database 218 may employ features of the computer operating system of the server 206. Database 218 may also utilize the file system via the computer operating system and may store and retrieve files stored in various formats. An RDBMS generally employs the Structured Query Language (SQL) in addition to a language for creating, storing, editing, and executing stored procedures.

Handheld user device 202 may be a smartphone (e.g., an APPLE IPHONE or SAMSUNG ANDROID smartphone) or a tablet. Handheld user device 202 includes display 220. Handheld device 202 also includes a microprocessor, volatile memory and non-volatile memory. Handheld device 202 also includes a communication interface. The communication interface is configured so that handheld user device 202 can transmit and receive data to and from breathing device 10 and can transmit and receive data to and from server 206. Breathing device 10 and handheld user device 202 may communicate with each other using a wireless protocol, such as BLUETOOTH protocol, ZIGBEE protocol, Wi-Fi and cellular. Handheld user device 202 may communicate with server 206 using the same wireless protocol or a different wireless protocol.

User computer 204 may be a desktop computer or notebook computer, for example. User computer 204 includes display 222. User computer 204 also includes a microprocessor, volatile memory and non-volatile memory. User computer also includes a communication interface. The communication interface is configured so that user computer 204 can transmit and receive data to and from breathing device 10 and can transmit and receive data to and from server 206. Breathing device 10 and user computer 204 may communicate with each other using a wireless protocol, such as BLUETOOTH protocol, ZIGBEE protocol, Wi-Fi and cellular. User computer 204 may communicate with server 206 using the same wireless protocol or a different wireless protocol.

The non-volatile and volatile memory of handheld user device 202 and user computer 204 may store and maintain computer-executable instructions, where the instructions may be executed by the microprocessor unit of handheld user device 202 and user computer 204, respectively. Such instructions and other data may be stored using a variety of computer-readable medium. The computer-readable medium (also referred to as a processor-readable medium or storage) includes any non-transitory (e.g., tangible) medium that participates in providing data (e.g., instructions) that may be read by a computer (e.g., by microprocessor unit of handheld user device 202 and user computer 204). In general, processors receive instructions, e.g., from the memory via the computer-readable storage medium, etc., and executes these instructions, thereby performing one or more processes, including one or more of the processes described herein. Computer-executable instructions may be compiled or interpreted from computer programs created using a variety of programming languages and/or technologies, including, without limitation, and either alone or in combination, Java, C, C++, C#, Fortran, Pascal, Visual Basic, Java Script, Perl, PL/SQL, etc. In one embodiment, the computer-executable instructions are compiled or interpreted from computer programs created in C#, .Net, Service Stack, SQL, PHP (for Linux) and/or ASP .Net (for Windows) and Rest API.

Server 206 includes network interface 210 that is configured to provide communication with network router 211. For example, network router 211 may be a wired or wireless Ethernet router. In some configurations, network router 211 may be further configured to provide a communication interface to external network 208. In some configurations, server 206 may exist as a remote server in a cloud computing architecture and may be referred to as a "cloud solution." In other configurations, server 206 may exist in a hosted environment where server 206 is local to users, e.g., without the use of external network 208, and may be referred to as a "hosted solution."

External network 208 may be referred to as the worldwide web or the Internet. External network 208 may establish a standard communication protocol between computing devices. External network 208 may permit information and data to be easily exchanged between computing devices and networks. Server 206 may host a website or webpage from which information may be derived. The information may be formatted for display on displays 220 and/or 222 of handheld user device 202 and/or user computer 204. Server 206 may include various types of computing apparatus, such as a computer workstation, a server, a desktop computer, a virtual server instance executed by a cluster or group of dedicated servers or computers, or some other computing system and/or device.

Handheld user device 202 and user computer 204 are examples of user devices that can be used by user 2 in connection with breathing device 10. A user device can be configured to receive data from breathing device 10. The data may include data regarding a user's breathing activities (e.g., inhales, exhales and holds after or between an inhale or exhale). These activities may be based on data regarding a breathing pattern transmitted to breathing device 10 from a user device or server 206. The breathing pattern may include a sequence of any two of the following: an inhale period, exhale period and hold period. The inhale period may be any of the following values or in a range of any two of the following periods: 1, 2, 3, 4, 5, 6, 7, 8, 9 and 10 seconds. The exhale period may be any of the following values or in a range of any two of the following periods: 1, 2, 3, 4, 5, 6, 7, 8, 9 and 10 seconds. The hold period may be any of the following values or in a range of any two of the following periods: 1, 2, 3, 4, 5, 6, 7, 8, 9 and 10 seconds. Breathing device 10 may be configured to transmit breathing activity data in real-time (e.g., immediately after the breathing activity is performed by the user, but not longer than 0.01, 0.05 or 0.1 seconds) to a user device. The breathing pattern data and breathing activity data can be stored in the memory of a user device and/or database 218.

Figure 9:
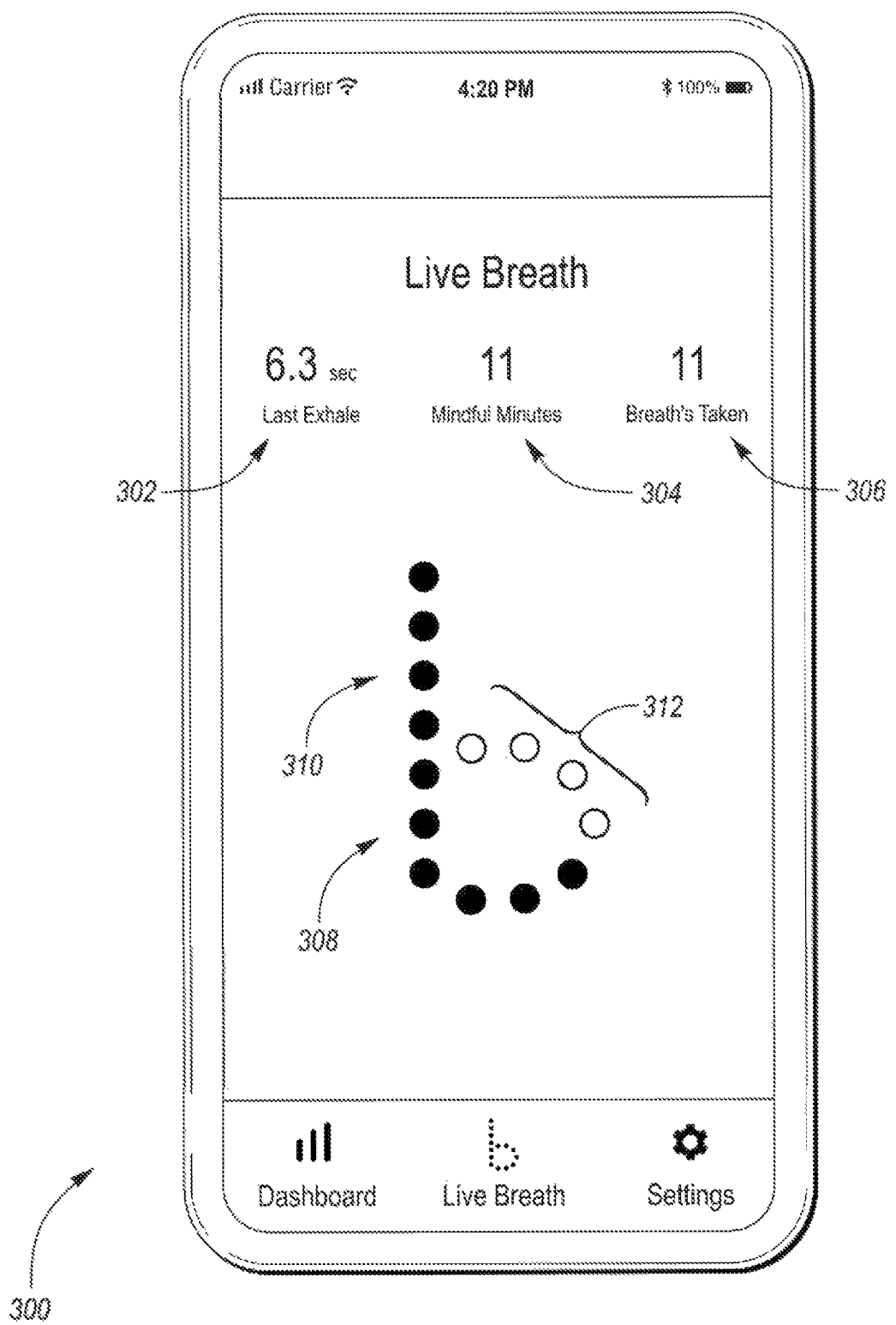
FIG. 9 depicts a computer user interface of a breathing system for displaying real-time breathing data according to one embodiment._

The microprocessor of a user device (e.g., handheld user device 202 and user computer 204) or server 206 may be configured to display a user interface including breathing activity data and breathing pattern data in real-time. FIG. 9 depicts a user interface 300 to display real-time breathing activity data. User interface 300 includes data fields 302, 304 and 306. Data field 302 may display the amount of time of the last breathing activity, e.g., last exhale, last inhale and last hold. As shown on user interface 300, data field 302 displays a last exhale of 6.3 seconds. Data field 304 may display the amount of time in which a user has participated in breathing sessions using breathing device 10 during the applicable period. As shown on user interface 300, this amount of time is represented as "mindful minutes." The "mindful minutes" value as shown on user interface 300 is 11 minutes. Data field 306 may display the number of breaths (e.g., each exhale, each inhale, or each pair of exhales and inhales) during the current breathing session using a breathing pattern or during a period, e.g., an hour, two hours, or a day. As shown on user interface 300, the number of breaths taken is 11.

User interface 300 also includes series of indicators 308. The configuration of the series of symbols 308 may be the same as the configuration of the series of apertures 46 of breathing device 10. For instance, the series of apertures 46 of breathing device 10 and the series of indicators 308 may form a "b" symbol. Series of indicators 308 may each change from a first state to a second state. As shown on user interface 300, first group of indicators 310 and second group of indicators 312 are in a first state and second state, respectively. The first state is a filled state and the second state is an unfilled state. In one embodiment, the first state corresponds to the operational state of a corresponding light emitter 74 and the second state corresponds to the non-operational state of a corresponding light emitter 74. In an embodiment, the state of each indicator in the series of indicators 308 can be the corresponding state of corresponding light emitter 74. For example, as shown in FIG. 9, the number of indicators in the first and second groups 310 and 312 corresponds to the amount light emitters 74 in the non-operational and operation states. This correspondence can be executed in real-time between a user device and breathing device 10, thereby synchronizing changes in the states of series of light emitters 74 and series of indicators 308. As one benefit, this permits the user to obtain real-time feedback regarding inhales, exhales and hold times of a breathing pattern in real-time from breathing device 10 and the user device simultaneously. As another benefit, the user can visualize and interact with its breathing data in real-time.

The microprocessor of handheld user device 202 may be configured to direct handheld user device 202 to transit auditory and/or vibratory signals as contemplated with those of breathing device 10. The signals of the two devices may be synchronized to provide a more interactive experience for the user.

Figure 10:
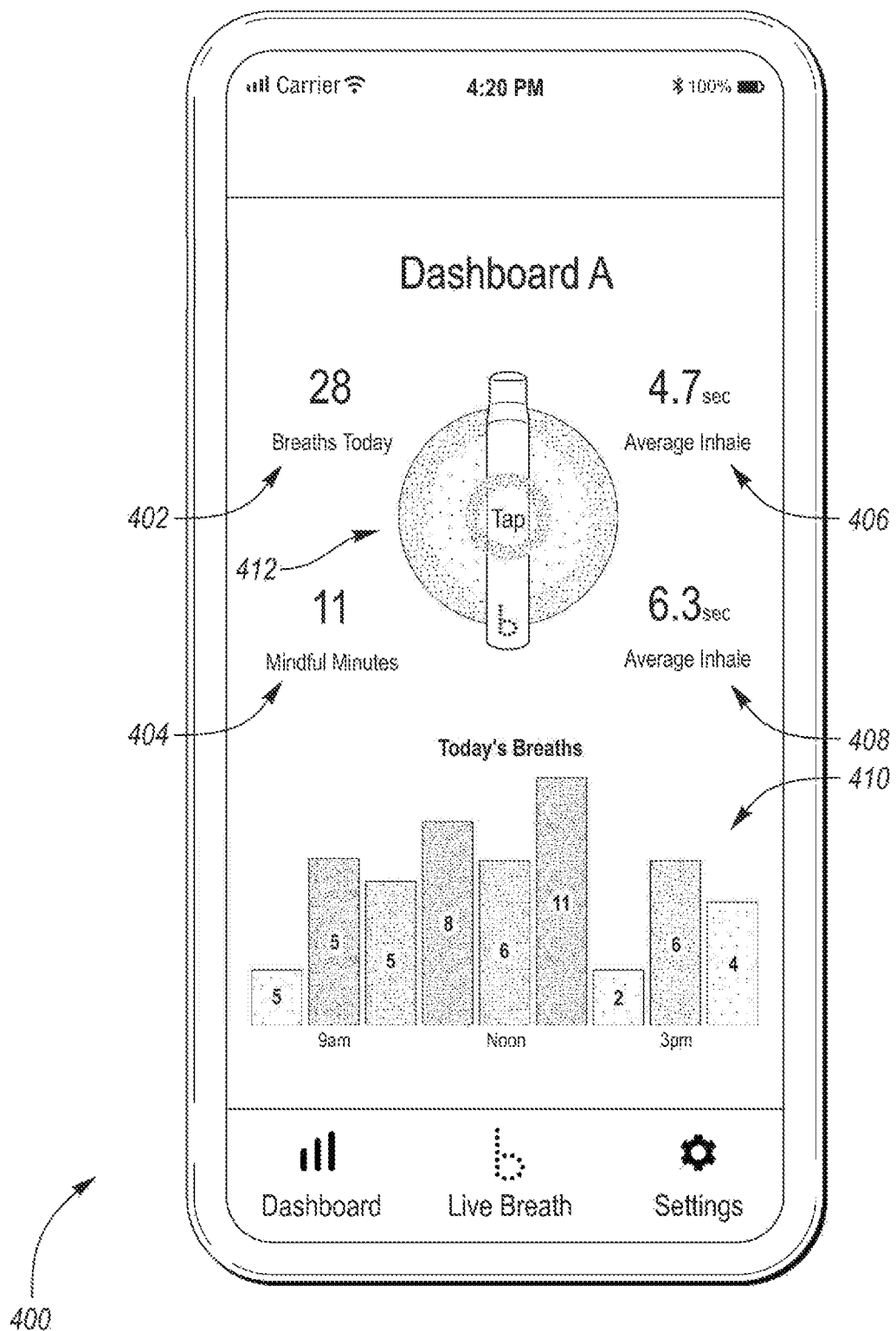
FIG. 10 depicts a computer user interface of a breathing system for displaying breathing data relating to a first user's breathing activity over a period of time according to one embodiment.

The microprocessor of a user device (e.g., handheld user device 202 and user computer 204) or server 206 may be configured to display a user interface including breathing activity data over a period, e.g., the last or current breathing session, the last or current day, the last or current week or the last or current month. The period can be otherwise selected by the user through input received by the user device or server 206. FIG. 10 depicts user interface 400 to display breathing activity data. User interface 400 includes data fields 402, 404, 406 and 408. Data field 402 may display the number of breaths taken during the applicable period. As shown on user interface 400, data field 402 displays 28 breaths during the current day. Data field 404 may display the amount of time in which a user has participated in breathing sessions using breathing device 10 during the applicable period. As shown on user interface 400, this amount of time is represented as "mindful minutes." The "mindful minutes" value as shown on user interface 400 is 11 minutes. Data field 406 displays the average inhale period for the inhales taken over the applicable period. As shown on user interface 400, the average inhale period is 4.7 seconds for the current day. Data field 408 displays the average exhale period for the exhales taken over the applicable period of time. As shown on user interface 400, the average inhale period is 6.3 seconds for the current day.

User interface 400 also includes a graphic 410 configured to display analytical data regarding the number of breaths during an applicable period. As shown on FIG. 10, the number of breaths per hour from 8 am to 4 pm are represented in graphic 410. In other embodiments, the applicable time period may vary (e.g., minute, day, month, etc.)

User interface 400 also includes a tap button 412. When tap button 412 is actuated by a user, a hot link to a settings menu is displayed. The content of the settings menu may be similar to the setting shown on user interface 700.

Figure 11:
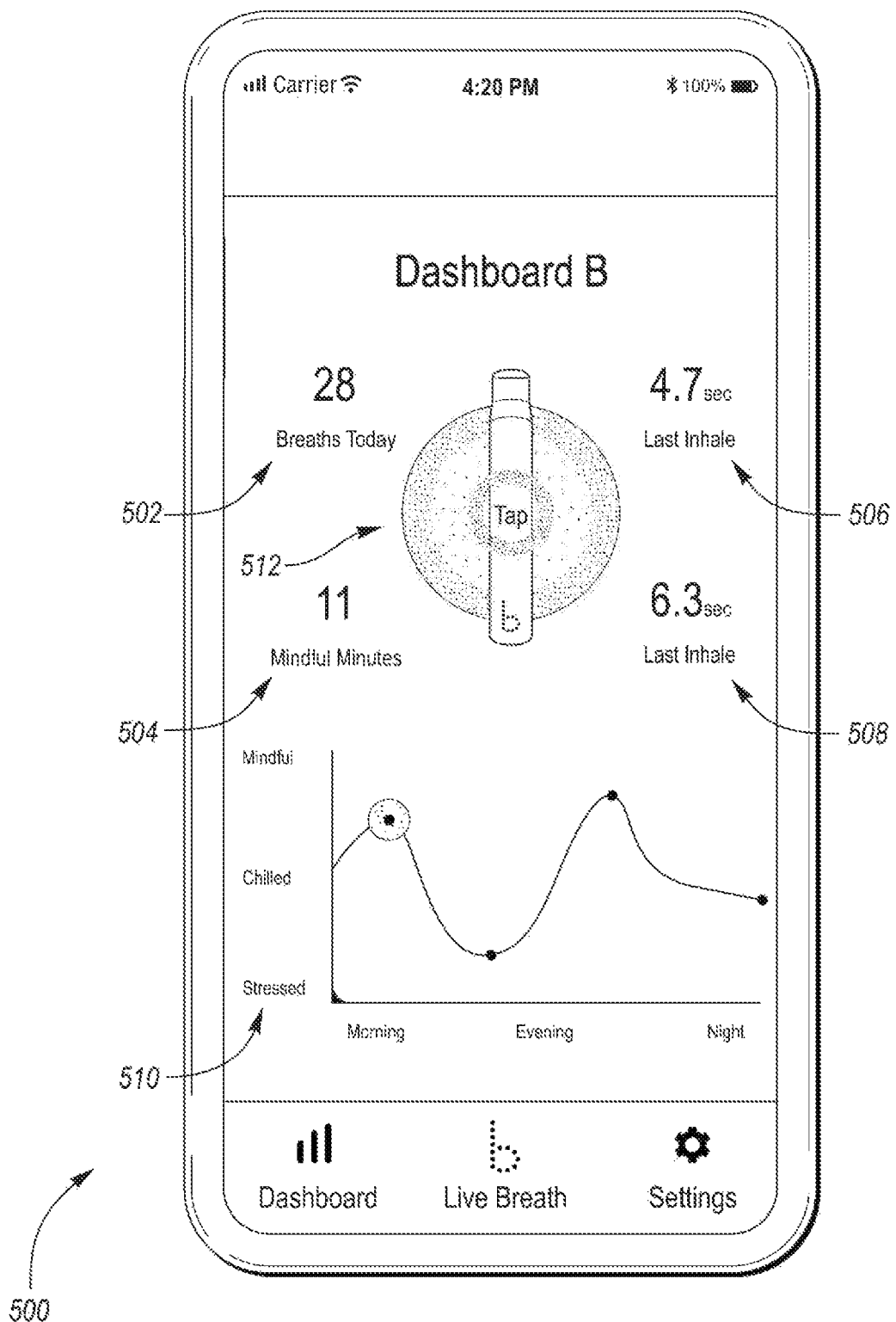
FIG. 11 depicts a computer user interface of a breathing system for displaying breathing data relating to a second user's breathing activity over a period of time according to one embodiment.

FIG. 11 depicts user interface 500 to display breathing activity data. User interface 500 includes data fields 502, 504, 506 and 508. Data field 502 may display the number of breaths taken during the applicable period. As shown on user interface 500, data field 502 displays 28 breaths taken during the current day. Data field 504 may display the amount of time in which a user has participated in breathing sessions using breathing device 10 during the applicable period. As shown on user interface 500, this amount of time is represented as "mindful minutes." The "mindful minutes" value as shown on user interface 500 is 11 minutes. Data field 506 displays the inhale period for the last inhale (alternatively, the user can select a different inhale). As shown on user interface 500, the last inhale period is 4.7 seconds. Data field 508 displays the average exhale period for the exhales taken over the applicable period. As shown on user interface 500, the last exhale period is 6.3 seconds.

User interface 500 also includes a graphic 510 configured to display analytical data regarding the number of breaths during an applicable period (e.g., morning, evening or night) that fall into the categories mindful, chilled and stressed.

User interface 500 also includes a tap button 512. When tap button 512 is actuated by a user, a hot link to a settings menu is displayed. The content of the settings menu may be similar to the setting shown on user interface 700.

Figure 12:
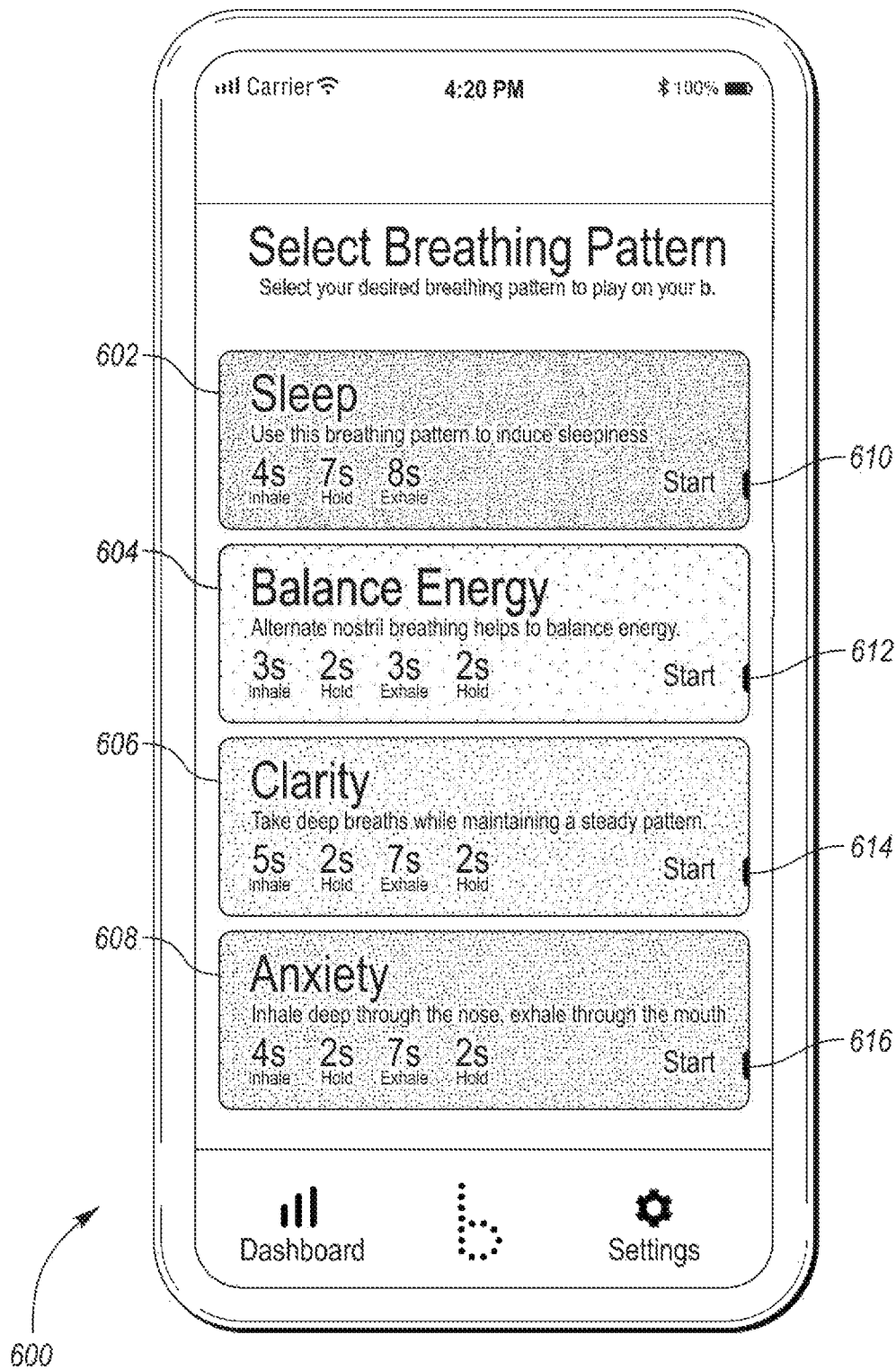
FIG. 12 depicts a computer user interface of a breathing system for indicating a pre-determined breathing pattern according to one embodiment.

The microprocessor of a user device (e.g., handheld user device 202 and user computer 204) or server 206 may be configured to display pre-determined breathing patterns (e.g., pre-determined by a factory manufacturing breathing device 10 or by a user) selectable by a user to be transmitted and executed on breathing device 10. Breathing device 10 is also configurable to execute a default breathing pattern if a user selected breathing pattern is not being used. The default breathing pattern may be stored on breathing device 10. FIG. 12 depicts user interface 600 to display user selectable pre-determined breathing patterns 602, 604, 606 and 608 and start buttons 610, 612, 614 and 616, respectively, to transmit the selected breathing pattern to breathing device 10 for execution. Breathing pattern 602 is a sleep breathing pattern configured to induce sleepiness of the user. Breathing pattern 602 includes the following sequence: a four (4) second inhale, a seven (7) second hold and an eight (8) second exhale. Breathing pattern 604 is a balance energy breathing pattern configured to alternate nostril breathing to balance energy. Breathing pattern 604 includes the following sequence: a three (3) second inhale, a two (2) second hold, a three (3) second exhale and a two (2) second hold. Breathing pattern 606 is a clarity breathing pattern configured to allow the user to take deep breaths while maintaining a steady pattern. Breathing pattern 606 includes the following sequence: a five (5) second inhale, a two (2) second hold, a seven (7) second exhale and a two (2) second hold. Breathing pattern 608 includes the following sequence: a four (4) second inhale, a two (2) second hold, a seven (7) second exhale, and a two (2) second hold. Additional breathing patterns may be unlocked during an in-app or online purchase.

Controller 56 of breathing device 10 is configured to control the sequence and timing of series of light emitters 74 during an inhale period, an exhale period and a hold period. In one embodiment, all or a portion thereof of light emitters in the series of light emitters 74 are non-operational during the start of an inhale period and all or a portion thereof of light emitters in the series of light emitters 74 are operational by the end of the inhale period. The timing of illumination may be at a regular interval. For instance, if the inhale period is eight (8) seconds and the number of light emitters 74 is sixteen (16), then each successive light emitter changes to the operational mode each 0.5 seconds (e.g., 16 light emitters/8 seconds). The timing of illumination may be at a non-regular interval, e.g., a first group of successive light emitters take longer or shorter to illuminate than a second group of successive light emitters. If the intervals are successively shorter, it can show the user that they are having success in coming closer and closer to achieving a successful inhale period. In one embodiment, all or a portion thereof of light emitters in the series of light emitters 74 are operational during the start of an exhale period and all or a portion thereof of light emitters in the series of light emitters 74 are non-operational by the end of the exhale period. The timing of turning off the light emitters 74 may be at a regular interval. For instance, if the exhale period is eight (8) seconds and the number of light emitters 74 is sixteen (16), then each successive light emitter changes to the non-operational mode each successive 0.5 second period (e.g., 16 light emitters/8 seconds). The timing of turning off the light emitters 74 may be at a non-regular interval, e.g., a first group of successive light emitters take longer or shorter to turn off than a second group of successive light emitters. If the intervals are successively shorter, it can show the user that she/he is having success in coming closer and closer to achieving a successful exhale period.

Controller 56 of breathing device 10 is configured to transmit real-time breathing data to user device and/or server 206, and those devices are configured to determine to what extent each inhale period, exhale period and hold period has been successfully completed (breathing device 10 may perform this function as well). The user device and/or server 206 may be configured to display successes and failures to provide a user feedback for future breathing exercises.

Figure 13:
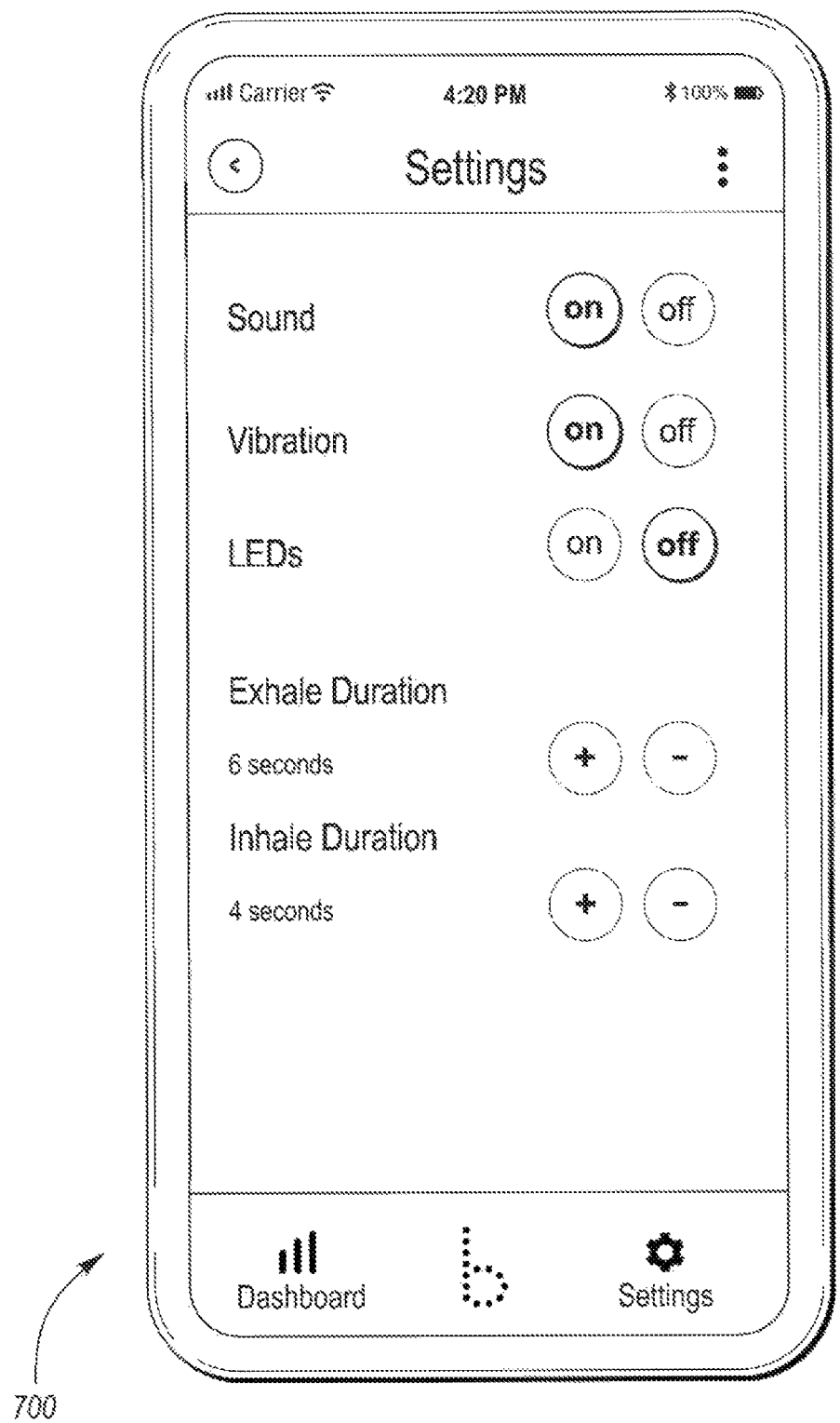
FIG. 13 depicts a computer user interface of a breathing system for indicating customizable settings of the breathing system according to one embodiment.

The microprocessor of a user device (e.g., handheld user device 202 and user computer 204) or server 206 may be configured to display user selectable settings and to receive input from user to change these settings. FIG. 13 depicts user interface 700 to display user selectable settings and to receive input from user to change these settings. These settings include sound on/off, vibration on/off, light emitters (LEDs) on/off. These settings further include the default inhale and exhale durations. These settings may further include a default hold period.

Non-volatile memory of a user device and/or database 218 may store data regarding breathing patterns, user activity (e.g., inhale, exhale and hold data) associated with user breathing exercises. The microprocessor of a user device (e.g., handheld user device 202 and user computer 204) or server 206 may be configured analyze this data to display through user interfaces 300, 400 and 500. Stored user activity may further include inhale and/or exhale force (e.g., strongest, average, etc.), longest and shortest inhale and exhale, average inhale and exhale, average length of breathing session and average number of breaths per session, day, week or month. Stored data may further include force expiratory volume in one (1) second (FEV1), forced vital capacity (FVC), inspiratory volume, and tidal volume.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

The following applications are related to the present application: U.S. patent application Ser. No. 16/358,034, filed on Mar. 19, 2019 and U.S. patent application Ser. No. 16/358,082, filed on Mar. 19, 2019, which are both incorporated by reference in their entirety herein.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A breathing device comprising:
 a housing portion having external and internal surfaces and a distal end portion and a proximal end portion; and
 a mouthpiece portion having external and internal surfaces and including a flared portion having a narrower distal end portion and extending to a wider proximal end portion, the narrower distal end portion is closer to the proximal end portion of the housing portion than the wider proximal end portion, the flared portion includes a depressed portion adjacent to the wider proximal end portion and configured to contact lips of a user, the flared portion having an outer surface, the depressed portion having a first surface and a second surface, the second surface extending between the outer surface of the flared portion and the first surface, the internal surface forming a mouthpiece portion cavity extending along a longitudinal axis of the mouthpiece portion, the mouthpiece portion including an extending portion concentrically located within the mouthpiece portion relative to the longitudinal axis of the mouthpiece portion, the extending portion extending beyond the wider proximal end portion of the mouthpiece portion and within the mouthpiece portion cavity, the extending portion configured to contact teeth of the user, and the wider proximal end portion of the mouthpiece portion and the extending portion forming an aperture therebetween configured to receive breaths.

2. The breathing device of claim 1, wherein the housing portion includes a first fitting disposed on the proximal end portion of the housing portion, the mouthpiece portion includes a second fitting disposed on the narrower distal end portion of the mouthpiece portion opposing the external or internal surface of the housing portion including the first fitting on the proximal end portion, and the second fitting configured to mate with the first fitting.

3. The breathing device of claim 1, wherein the housing portion and the mouthpiece portion form a single, unitary component of the breathing device.

4. The breathing device of claim 1, wherein a surface of the depressed portion has a texture different than a surface of the remaining flared portion.

5. The breathing device of claim 4, wherein the depressed portion surface has a glossy texture and the remaining flared portion surface has a knurled surface.

6. The breathing device of claim 1, wherein the depressed portion including first and second opposing depressed portions.

7. The breathing device of claim 1, wherein the first surfaces has first and second lateral sides terminating in the outer surface of the flared portion.

8. A breathing device comprising:
 a housing portion having external and internal surfaces and a distal end portion and a proximal end portion; and
 a mouthpiece portion having external and internal surfaces and a distal end portion and a proximal end portion, the internal surface forming a mouthpiece portion cavity extending along a longitudinal axis of the mouthpiece portion, the mouthpiece portion including an extending portion concentrically located within the mouthpiece portion relative to the longitudinal axis of the mouthpiece portion, the extending portion extending beyond the proximal end portion of the mouthpiece portion and within the mouthpiece portion cavity, the extending portion configured to contact teeth of a user, and the proximal end portion of the mouthpiece portion and the extending portion forming an aperture therebetween configured to receive breaths.

9. The breathing device of claim 8, wherein the housing portion includes a first fitting disposed on the proximal end portion of the housing portion, the mouthpiece portion includes a second fitting disposed on the distal end portion of the mouthpiece portion opposing the external or internal surface of the housing portion including the first fitting on the proximal end portion, and the second fitting configured to mate with the first fitting.

10. The breathing device of claim 8, wherein the housing portion and the mouthpiece portion form a single, unitary component of the breathing device.

11. The breathing device of claim 8, wherein the extending portion includes an enlarged base portion and an enlarged head portion defining a groove portion therebetween configured to contact the teeth of the user.

12. The breathing device of claim 11, wherein the enlarged head portion is spaced apart from the proximal end portion of the mouthpiece portion.

13. The breathing device of claim 8, wherein the extending portion is connected to the internal surface of the mouthpiece portion.

14. The breathing device of claim 8, wherein the mouthpiece portion includes a number of struts situated within the aperture and connecting the extending portion to the internal surface of the mouthpiece portion.

15. The breathing device of claim 8, wherein the extending portion includes a groove portion bounded by an enlarged base portion and an enlarged head portion having a curved upper surface.

16. A breathing device comprising:
a housing having external and internal surfaces, the housing including a housing cavity, the housing includes a series of light emitters forming a first symbol; and
a mouthpiece portion having external and internal surfaces and having a passage therein configured to receive breaths including inhales and exhales, the internal surface forming a mouthpiece portion cavity extending along a longitudinal axis of the mouthpiece portion, the mouthpiece portion including an extending portion concentrically located within the mouthpiece portion relative to the longitudinal axis of the mouthpiece portion, the extending portion extending beyond a proximal end portion of the mouthpiece portion and within the mouthpiece portion cavity, the extending portion configured to contact teeth of a user, and the proximal end portion of the mouthpiece portion and the extending portion forming an aperture therebetween configured to receive breaths; and
a series of apertures formed in the housing such that each aperture is spaced apart from an adjacent aperture by a portion of the housing, the series of light emitters are aligned with the series of apertures.

17. The breathing device of claim 16, wherein the series of light emitters are aligned with the series of apertures such that each light emitter in the series of light emitters is arranged under a distinct aperture such that when each light emitter is illuminated, light is directed through the distinct aperture and not other apertures.

18. The breathing device of claim 16, wherein the external surface of the mouthpiece portion has an embossment forming a second symbol.

19. The breathing device of claim 18, wherein the first symbol is a letter.

20. The breathing device of claim 18, wherein the first symbol is a logo.

21. The breathing device of claim 16, wherein the series of light emitters is a series of light emitting diodes (LEDs).

* * * * *